(12) United States Patent
Bolduc

(10) Patent No.: US 7,559,968 B2
(45) Date of Patent: *Jul. 14, 2009

(54) MICROBICIDAL AIR FILTER

(75) Inventor: Normand Bolduc, Laval (CA)

(73) Assignee: Noveko Inc., Terrebonne, Quebec (CA)

( * ) Notice: Subject to any disclaimer, the term of this patent is extended or adjusted under 35 U.S.C. 154(b) by 129 days.

This patent is subject to a terminal disclaimer.

(21) Appl. No.: 10/455,337

(22) Filed: Jun. 6, 2003

(65) Prior Publication Data

US 2003/0205137 A1 Nov. 6, 2003

Related U.S. Application Data

(63) Continuation-in-part of application No. 09/982,804, filed on Oct. 22, 2001, now abandoned.

(51) Int. Cl.
*B01D 39/02* (2006.01)

(52) U.S. Cl. ............... 55/524; 55/527; 55/DIG. 5; 55/385.1; 95/211; 96/154; 96/290; 96/296; 261/104; 261/107; 422/120

(58) Field of Classification Search ............... 55/522, 55/508, 511, 518, DIG. 35, 524, 527, DIG. 5, 55/385.1; 96/223, 226, 134, 181, 154, 296, 96/290, 227; 602/26, 63; 128/205.27, 205.28, 128/201.25; 95/170, 211; 428/372; 423/237; 261/104, 107; 422/120, 4

See application file for complete search history.

(56) References Cited

U.S. PATENT DOCUMENTS

| | | | |
|---|---|---|---|
| 1,319,763 A | | 10/1919 | Drew |
| 3,017,239 A | * | 1/1962 | Rodman ............ 96/226 |
| 3,451,392 A | * | 6/1969 | Cook et al. ........ 128/206.11 |
| 3,457,917 A | * | 7/1969 | Mercurio ............ 128/204.12 |
| 3,710,948 A | | 1/1973 | Sexton |
| 3,779,244 A | | 12/1973 | Weeks |
| 3,802,429 A | | 4/1974 | Bird |
| 3,823,533 A | | 7/1974 | Alverson et al. |
| 4,197,100 A | | 4/1980 | Hausheer |
| 4,519,823 A | | 5/1985 | Kinney et al. |
| 4,798,676 A | | 1/1989 | Matkovich |

(Continued)

FOREIGN PATENT DOCUMENTS

EP 0958851 11/1999

(Continued)

OTHER PUBLICATIONS

Webster's Ninth New Collegiate Dictionary, A Merriam-Webster Publisher, Inc, p. 606, Definition of "Impregnate".*

(Continued)

*Primary Examiner*—Duane Smith
*Assistant Examiner*—Minh-Chau T Pham
(74) *Attorney, Agent, or Firm*—Klarquist Sparkman, LLP

(57) ABSTRACT

Microbicidal air filter for use with an air passageway, which includes an immobilization network including fibers having substantially embodied therein an amount of at least one antimicrobial agent sufficient to substantially immobilize, retain and kill microbes suspended in a volume of air moving through the air passageway. The immobilization network is substantially permeable to air. A microbicidal facemask and a microbicidal air filter used in an air circulation system using the immobilization network are disclosed.

68 Claims, 4 Drawing Sheets

U.S. PATENT DOCUMENTS

| | | | |
|---|---|---|---|
| 4,856,509 A | | 8/1989 | Lemelson |
| 4,977,634 A | * | 12/1990 | Koji ............................... 5/638 |
| 5,165,395 A | * | 11/1992 | Ricci ..................... 128/202.22 |
| 5,525,136 A | | 6/1996 | Rosen |
| 5,704,966 A | * | 1/1998 | Rohrbach et al. ............. 95/170 |
| 5,713,971 A | * | 2/1998 | Rohrbach et al. ............. 96/181 |
| 5,744,236 A | * | 4/1998 | Rohrbach et al. ........... 428/372 |
| 5,747,053 A | | 5/1998 | Nashimoto |
| 5,759,394 A | * | 6/1998 | Rohrbach et al. ........... 210/264 |
| 5,876,489 A | | 3/1999 | Kunisaki et al. |
| 5,902,384 A | * | 5/1999 | Rohrbach et al. ............. 96/296 |
| 5,906,677 A | | 5/1999 | Dudley |
| 5,951,744 A | * | 9/1999 | Rohrbach et al. ............. 96/154 |
| 6,036,738 A | * | 3/2000 | Shanbrom .................... 55/524 |
| 6,045,820 A | | 4/2000 | Messier |
| 6,063,170 A | | 5/2000 | Deibert |
| 6,224,655 B1 | | 5/2001 | Messier |
| 6,514,306 B1 | * | 2/2003 | Rohrbach et al. ............. 55/524 |
| 6,562,885 B1 | | 5/2003 | Moorehead et al. |
| 6,592,861 B2 | | 7/2003 | Messier |
| 6,645,447 B2 | * | 11/2003 | Rohrbach et al. ........... 423/237 |
| 6,726,751 B2 | * | 4/2004 | Bause et al. .................. 96/134 |
| 6,742,518 B2 | * | 6/2004 | Chang .................. 55/DIG. 35 |
| 6,872,241 B2 | * | 3/2005 | Soane et al. .................. 96/226 |
| 7,044,993 B1 | * | 5/2006 | Bolduc ........................ 55/524 |
| 2003/0075047 A1 | | 4/2003 | Bolduc |
| 2003/0116022 A1 | * | 6/2003 | Kritzler ....................... 96/226 |
| 2003/0205137 A1 | | 11/2003 | Bolduc |
| 2004/0250683 A1 | * | 12/2004 | Soane et al. .................. 96/226 |

FOREIGN PATENT DOCUMENTS

| | | |
|---|---|---|
| FR | 2804032 | 7/2001 |
| JP | 2088083 | 3/1990 |
| JP | 9084890 | 3/1997 |
| JP | 10033701 | 2/1998 |

OTHER PUBLICATIONS

Amendment A filed with the U.S. Patent and Trademark Office for a U.S. Reexamination U.S. Appl. No. 90/009,141, dated Jan. 21, 2009.

Amendment A - Supplemental filed with the U.S. Patent and Trademark Office for U.S. Reexamination U.S. Appl. No. 90/009,141, dated Jan. 22, 2009.

Amendment B filed with the U.S. Patent and Trademark Office for U.S. Reexamination U.S. Appl. No. 90/009,141, dated Mar. 12, 2009.

Office Action from U.S. Patent and Trademark Office for U.S. Reexamination U.S. Appl. No. 90/009,141, dated Nov. 20, 2008.

Office Action from the European Patent Office for European Patent Application No. 03817122.9, dated Mar. 13, 2009.

Order Granting Reexamination for U.S. Reexamination U.S. Appl. No. 90/009,141, dated Jul. 22, 2008.

Request for Reexamination of U.S. Patent No. 7,044,993, dated May 6, 2008.

* cited by examiner

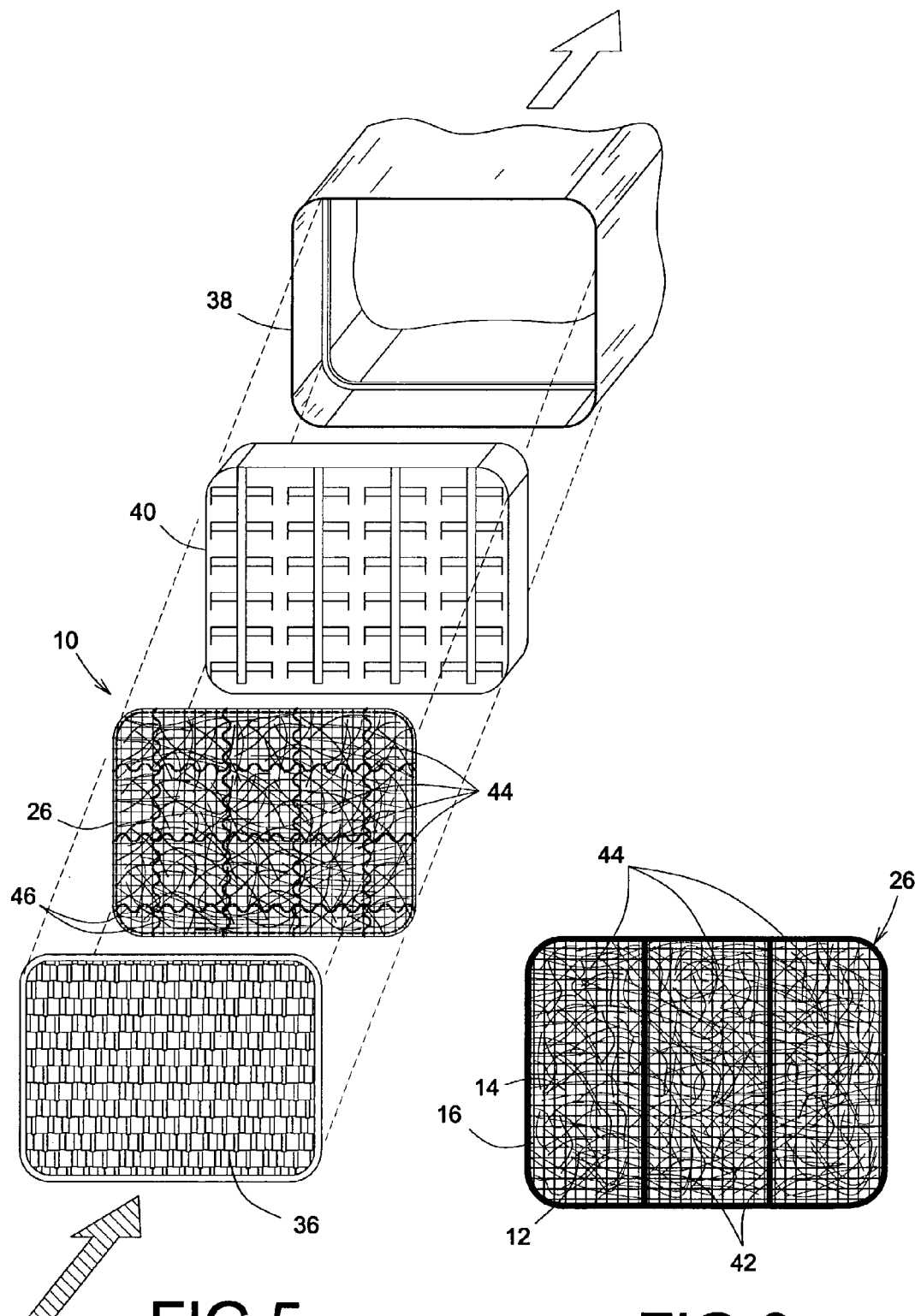

MICROBICIDAL AIR FILTER

CROSS REFERENCE TO RELATED APPLICATIONS

This application is a continuation-in-part (C.I.P.) of application Ser. No. 09/982,804, filed on Oct. 22, 2001, now abandoned.

FIELD OF THE INVENTION

The present invention concerns air filters, more particularly microbicidal air filters.

BACKGROUND OF THE INVENTION

Removing airborne pathogens and environmental allergens is very important in environments that require high levels of air purity, such as in hospitals and in houses of people suffering from severe allergic responses to the aforesaid allergens. Typically, devices in the form of masks or in-air duct filters filter out particulate material during either air circulation or, in the case of facemasks, during inhalation and exhalation. The facemasks and air duct filters temporarily capture the pathogens and allergens, and particulate matter such as dust, on a surface of a filtering material. Once the filters reach a threshold limit or after a single use, they are typically discarded or in some cases, cleaned and reused. Many designs of filtering devices exist, examples of which are as follows:

U.S. Pat. No. 1,319,763, issued Oct. 28, 1919, to Drew for "Air filter for wall registers";

U.S. Pat. No. 3,710,948, issued Jan. 16, 1973, to Sexton for "Self-sustaining pocket type filter";

U.S. Pat. No. 3,779,244, issued Dec. 18, 1973, to Weeks for "Disposable face respirator";

U.S. Pat. No. 3,802,429, issued Apr. 9, 1974, to Bird for "Surgical face mask";

U.S. Pat. No. 4,197,100, issued Apr. 8, 1980, to Hausheer for "Filtering member for filters";

U.S. Pat. No. 4,798,676, issued Jan. 17, 1989, to Matkovich for "Low pressure drop bacterial filter and method";

U.S. Pat. No. 5,525,136, issued Jun. 11, 1996, to Rosen for "Gasketed multi-media air cleaner";

U.S. Pat. No. 5,747,053 issued May 5, 1998, to Nashimoto for "Antiviral filter air cleaner impregnated with tea extract"; and U.S. Pat. No. 5,906,677, issued May 25, 1999, to Dudley for "Electrostatic supercharger screen".

The aforesaid designs suffer from a number of important drawbacks. Disadvantageously, in the above-mentioned designs removal of the dirty filter or the facemask after use may cause non-immobilized pathogens or particulates to be dispersed into the air immediately around the user, which, if inhaled may be hazardous to the user. In addition, the designs may not immobilize the air borne pathogens and kill them in situ. Some of the designs incorporate viscous material into the filter material to capture particulate material. Some designs incorporate complex arrangements of filters inside cartridges, which may be impractical for use in air ducts or in facemasks. In some cases, fiberglass is used as part of the filter medium, which may be harmful to humans if located near the nose and mouth. In one design, disinfectant soaked cotton wool appears to be located in an air duct for aerosolizing into a room to maintain moisture content. Use of such a wet disinfectant may be harmful to humans in close proximity to the disinfectant and may not be appropriate for use in a facemask.

Further advantages of the invention will be in part obvious from an inspection of the accompanying drawings and a careful consideration of the following description.

SUMMARY OF THE INVENTION

The present invention reduces the difficulties and disadvantages of the prior art by providing a microbicidal air filter, which captures and kills pathogenic microbes on a novel immobilization network of fibers. To achieve this, the fibers include an antimicrobial agent within their structure (impregnated or embodied therein), which substantially kills the microbes and retains them within the body of the fibers. This significantly reduces or essentially eliminates the problems associated with further release of the microbes from the filter after use and during disposal. Advantageously, the filter can be used as a facemask or in air-circulation ducts, typically as an after-filter or downstream of a filter, and can capture and kill a wide variety of microbes. Desirably, the fibers can be made of a material, which enables the filter to be washed and reused without significant loss of antimicrobial activity Accordingly, in a first embodiment of the present invention, there is provided a microbicidal air filter for use with an air passageway, said air filter comprising: an immobilization network including fibers having substantially embodied therein an amount of at least one antimicrobial agent sufficient to substantially immobilize, retain and kill microbes suspended in a volume of air moving through said air passageway, said immobilization network being substantially permeable to said air.

Accordingly, in a second embodiment of the present invention, there is provided a microbicidal air filter for use with an air passageway, said air filter comprising: an immobilization network including fibers having substantially embodied therein an amount of at least one antimicrobial agent sufficient to substantially immobilize, retain and substantially inhibit the growth of microbes suspended in a volume of air moving through said air passageway, said immobilization network being substantially permeable to said air.

Accordingly, in a third embodiment of the present invention, there is provided a microbicidal face mask comprising: first and second air permeable screen elements secured together along respective peripheral edges, said screen elements defining a gap therebetween, said screen elements being configured and sized to fit over the mouth and nose of a user and to be secured thereto; an air permeable immobilization network located in and substantially filling said gap, said immobilization network including fibers having substantially embodied therein an amount of at least one antimicrobial agent sufficient to substantially immobilize, retain and kill microbes suspended In a volume of air moving through said network.

Accordingly, in a fourth embodiment of the present invention, there is provided a microbicidal face mask comprising: first and second air permeable screen elements secured together along respective peripheral edges, said screen elements defining a gap therebetween, said screen elements being configured and sized to fit over the mouth and nose of a user and to be secured thereto; an air permeable immobilization network located in and substantially filling said gap, said immobilization network including fibers having substantially embodied therein an amount of at least one antimicrobial agent sufficient to substantially immobilize, retain and substantially inhibit the growth of microbes suspended in a volume of air moving through said network.

Accordingly, in a fifth embodiment of the present invention, there is provided a microbicidal air duct filter for use in an air circulation system, said air duct filter comprising: first and second air permeable screen elements securable together along respective peripheral edges, said screen elements being configured and sized to fit in an air duct and to be secured therein; an air permeable immobilization network located substantially between said first and second screen elements, said immobilization network including fibers having substantially embodied therein an amount of at least one antimicrobial agent sufficient to substantially immobilize, retain and kill microbes suspended in a volume of air moving through said network.

Accordingly, in a sixth embodiment there is provided a microbicidal air duct filter for use in an air circulation system, said air duct filter comprising: first and second air permeable screen elements securable together along respective peripheral edges, said screen elements being configured and sized to fit in an air duct and to be secured therein; an air permeable immobilization network located substantially between said first and second screen elements, said immobilization network including fibers having substantially embodied therein an amount of at least one antimicrobial agent sufficient to substantially immobilize, retain and substantially inhibit the growth of microbes suspended in a volume of air moving through said network.

BRIEF DESCRIPTION OF THE DRAWINGS

In the annexed drawings, like reference characters indicate like elements throughout.

FIG. 5 is a simplified exploded view of an air circulation system with a filter;

FIG. 6 is simplified front view of an alternative filter for use in the system of FIG. 5;

DETAILED DESCRIPTION OF THE INVENTION

With reference to the annexed drawings the preferred embodiments of the present invention will be herein described for indicative purposes and by no means as of limitation.

Definitions

As used herein, the term "microbe" or "microbial" is intended to mean microorganisms including, but not limited to, bacteria, protozoa, viruses, molds and the like. Also included in this definition are dust mites.

As used herein, the term "antimicrobial agent" is intended to mean a compound that inhibits, prevents, or destroys the growth or proliferation of microbes such as bacteria, protozoa, viruses, molds and the like. Examples of antimicrobial agents as used herein include anti-bacterial agents, anti-viral agents, anti-mold agents, anti-yeast agents and anti-dust mite agents, or any combination thereof.

As used herein, the term "anti-bacterial agent" is intended to mean a compound that inhibits, prevents the growth of, or kills bacteria.

As used herein, the term "anti-viral agent" is intended to mean a compound that inhibits, prevents the growth of, or kills viruses.

As used herein, the term "anti-mold agent" is intended to mean a compound that inhibits, prevents the growth of, or kills molds.

As used herein, the term "anti-yeast agent" is intended to mean a compound that inhibits, prevents the growth of, or kills yeasts.

As used herein, the term "anti-dust mite agent" is intended to mean a compound that inhibits, prevents the growth of, or kills dust mites.

As used herein, the term "microbicidal" is intended to refer to the inhibition, growth prevention or killing properties of any of the aforesaid "agents", used either alone or in combination with each other.

Preferred Embodiments

Figure 1:
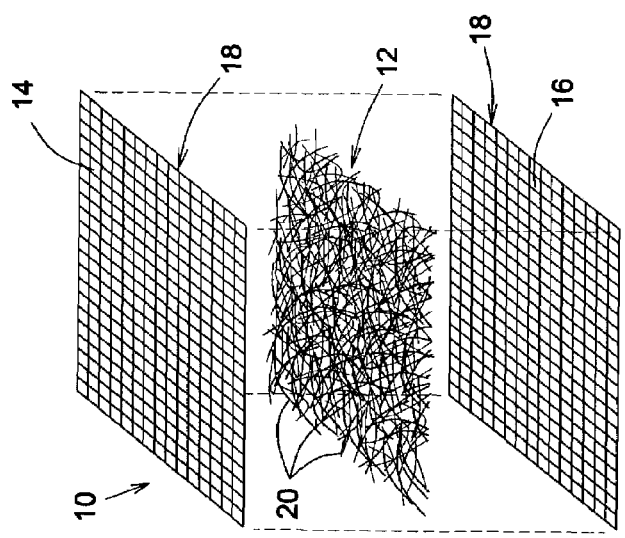
FIG. 1 is a simplified exploded view of an embodiment of a filter.

Referring now to FIG. 1, a first embodiment of a microbicidal air filter shown generally at 10. Broadly speaking, the filter 10 includes an air permeable immobilization network 12, an air permeable first screen 14 and an air permeable second screen 16. The first screen 14 and the second screen 16 are merely acting to support the network 12 and to define a work area 18. One skilled in the art will recognize that the immobilization network 12 may be used independently of the screens 14 and 16.

The network 12 includes a mesh of fibers 20, which can be non-woven or woven depending on whether a soft or hard (rigid) network is desired. The network 12 may also include yarn such as cotton in which the fibers 20 are interwoven. Each fiber 20 includes a quantity of at least one antimicrobial agent that is fully impregnated and integral with the body of the fiber 20 thereby providing a large concentration of the antimicrobial agent over a large surface area. The fibers 20 are arranged such that they are permeable to air over the entire mesh, typically as a fine layer of so-called angels hair, of flaky mesh or the like.

Preferably, the network is a fibrous material. More preferably, the fibrous material is commercially available RHOVYL’A.S.+™, RHOVYL’As™, THERMOVYL-ZCB™, THERMOVYL-MXB™ or TRICLOSAN™ treated PVC organic fiber.

Both RHOVYL’A.S.+™, RHOVYL’As™, THERMOVYL-MXB™ and THERMOVYL-ZCB™ are fibrous material that have instrinsic antimicrobial activity. In particular, the RHOVYL’As™ fiber and the THERMOVYL-ZCB™ fiber contain an antibacterial agent, which is integrated, or impregnated therein, (embodied) therein, in the body of the fiber, whereas the RHOVYL’A.S.+™ fiber antibacterial agent, the RHOVYL’A.S.+™ fiber and the THERMOVYL-MXB™ fiber also contain acaricide, an anti-dust mite agent. TRICLOSAN™ is an antimicrobial agent, which reduces the growth or kills microbes such as bacteria, yeast and molds.

The fibrous material is either used pure (100%) or in blends, with a percentage of at least 30% volume, along with other types of fibers within woven or non-woven type fabrics, and which meet the requirements of an individual protective equipment (IPE). The fibrous material may also have other properties including, but not limited to, non-flammability, resistance to chemical products, ignition suppression, thermal insulation, and moisture management.

Preferably, the antimicrobial agents include an antibacterial agent, an anti-viral agent, an anti-dust mite agent, an anti-mold agent and an anti-yeast agent.

Preferably, the anti-bacterial agent is TRICLOSAN™.

Preferably, the anti-dust mite agent is benzyl benzoate.

Typically, the fibrous material has porosity in the range of about 0.1 µm to about 3 µm, although this depends upon the size of microbe to be retained.

Typically, the fibrous material has a density of between two grams per square foot (2 gr/ft$^2$) to thirty grams per square foot (30 gr/ft$^2$). More preferably, the density is around ten grams per square foot (10 gr/ft$^2$).

Figure 2A:
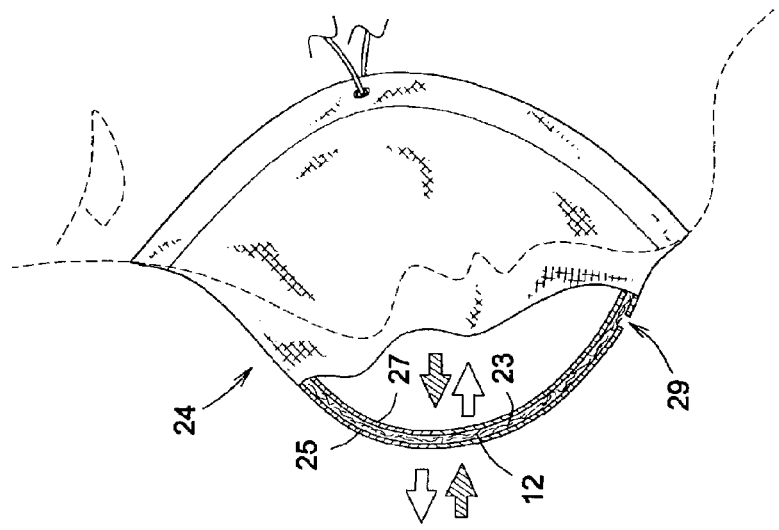
FIG. 2a is a simplified partial cutaway view of an alternative embodiment of a facemask.
Figure 2:
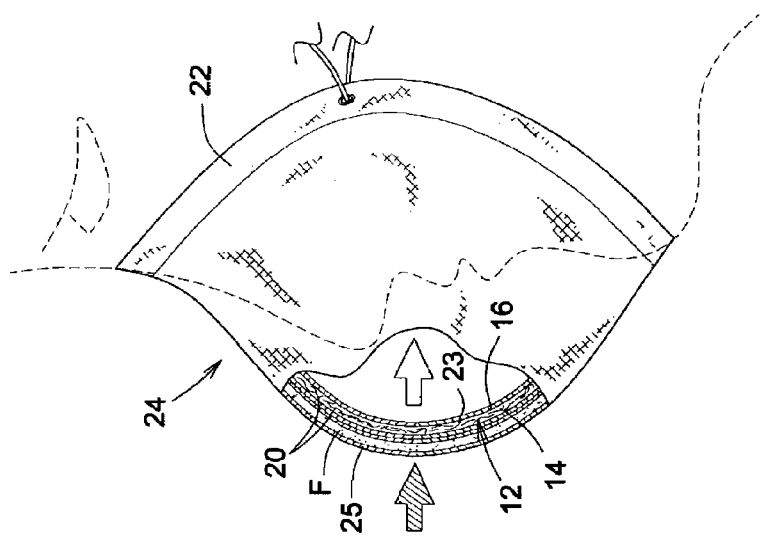
FIG. 2 is a simplified partial cutaway view of a facemask with the filter.

As best illustrated in FIG. 2, the filter 10 may be part of a facemask 24 of the type normally used by hospital workers and the like and which could be expandable (soft mask) or not (rigid mask), that are sometimes used in areas with pre-filtered air. The screens 14 and 16 are typically connected around a peripheral edge 22 and define a gap 23 therebetween. The network 12 can be attached to one of the aforesaid screens to provide both a physical barrier against particulate material and more importantly, to pathogenic microbes. The network 12 can be attached to the screens 14 or 16 using a VELCRO™ type fastener, stitches, bonding and the like, or inside an individual portable mask 24 that are worn in front of the nose/mouth area of the individual. A front mask screen 25 of the mask 24 acts as a primary filter located upstream of the network 12 to pre-filter the air by removing particulate material and microbes from the air passing therethrough along an air passageway, as shown by the arrows.

Alternatively, as best illustrated in FIG. 2a, the network 12 may be located between the front screen 25 and a rear screen 27, such as commercially available filter masks, in the gap 23 of the facemask 24 to create a two-way system of filtration, as shown by the arrows. The front screen 25 may include a slit 29 to allow the network 12 to be inserted into the gap 23. This type of facemask 24 may be useful for people who are suffering from a respiratory infection and who still wish to work yet, don't wish to infect others by exhaling breath contaminated with pathogenic microbes.

Figure 4:
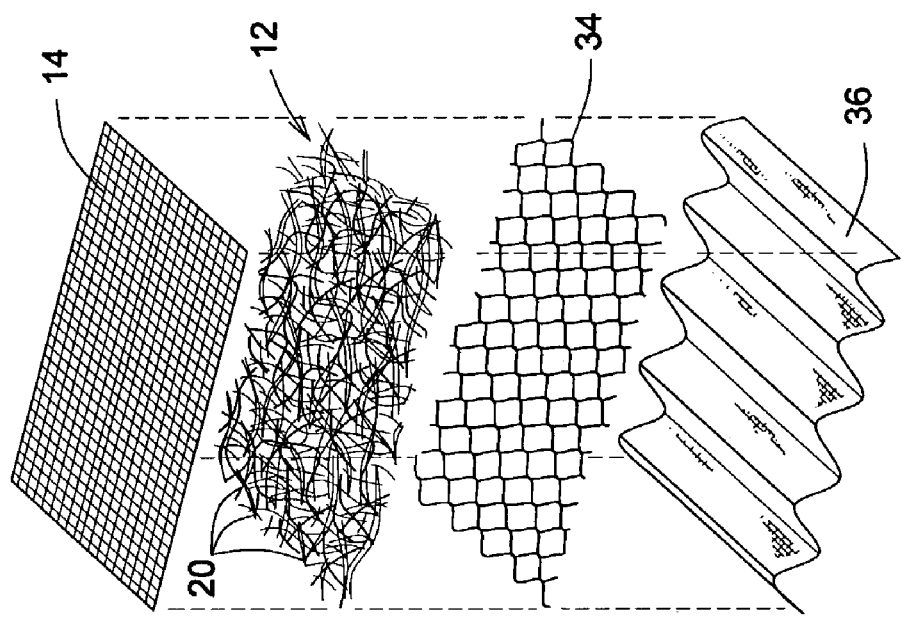
FIG. 4 is a simplified exploded view of the filter with a primary filter.
Figure 3:
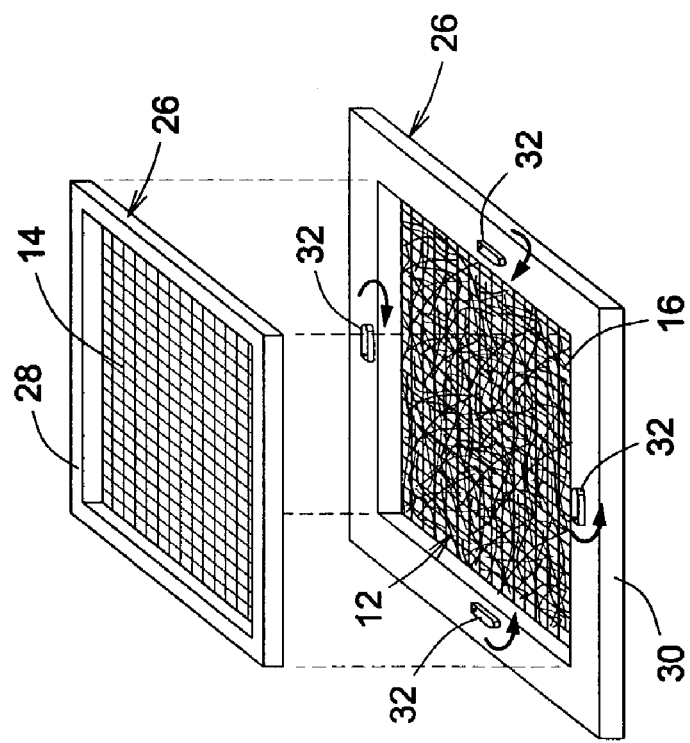
FIG. 3 is a simplified exploded view of an embodiment of a filter in a frame.
Figure 7:
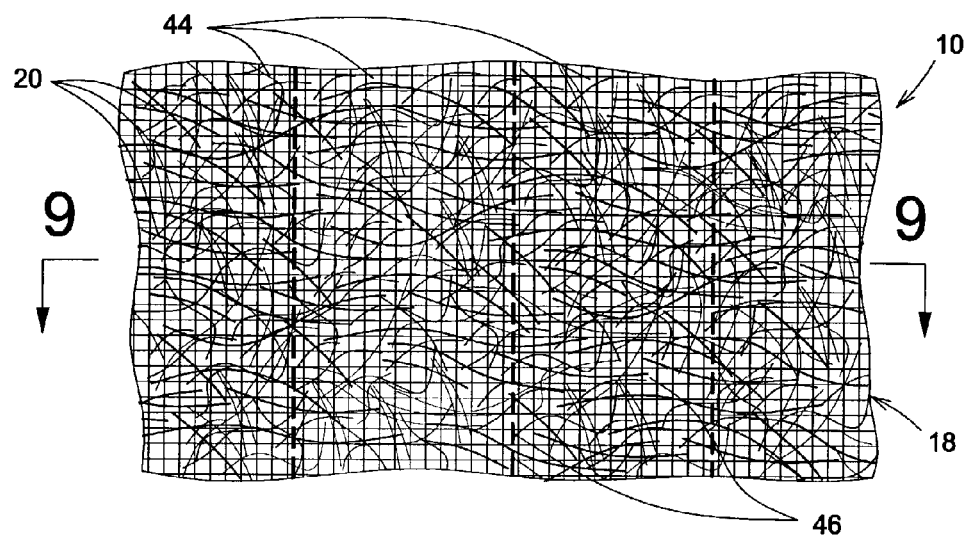
FIG. 7 is a simplified front view of an alternative filter for use with the system of FIG. 5, showing stitches as a fastening member.

The screen elements 14, 16 can have different sizes and shapes and can be simple typical flexible or semi-flexible type screens as illustrated in FIG. 1, made from aluminum, nylon, thermoplastic material, fiberglass type materials (usually not approved for mask applications), woven type fabrics or the like. As shown in FIG. 3, the screen elements 14, 16 and the network 12 can be supported by a rigid frame 26, such as a standard aluminum screen frame, that is divided into two parts 28, 30 and integral with the screen elements 14, 16 respectively, to ensure rigidity and ease of installation. A fastening member 32 may be used to releasably connect the two screen elements 14, 16 together with the network 12 sandwiched therebetween and compressed to prevent it from being displaced by the air flowing therethrough. The fastening member 32 may be a pivoting retainer pivoting on one of the parts 28, 30 to retain the other part against the same. Alternatively, as best illustrated in FIG. 4, a rigid screen 34 of any existing air filter 36 may also be used.

Referring now to FIGS. 5 and 6, the filter 10 is illustrated installed inside an air duct 38 downstream of the air filter 36 and upstream of an air heating system 40 (the arrows in FIG. 5 show the air passageway) such that the air passing through the network 12 is pre-filtered. The frame 26 generally encloses the screen elements 14, 16 but also includes intermediate reinforcing rods 42 used to subdivide the screen elements 14, 16 into a plurality of smaller sub-elements 44 to constrain the network 12 to remain in place between the two elements 14, 16. Alternatively, as best seen in FIG. 6, the frame 26 is a thin metallic rod onto which the screens 14, 16 are attached, with reinforcing rods 42 providing additional support to the screen elements 14, 16 and to the network 12 and to provide the aforesaid sub-elements 44.

Figure 8:
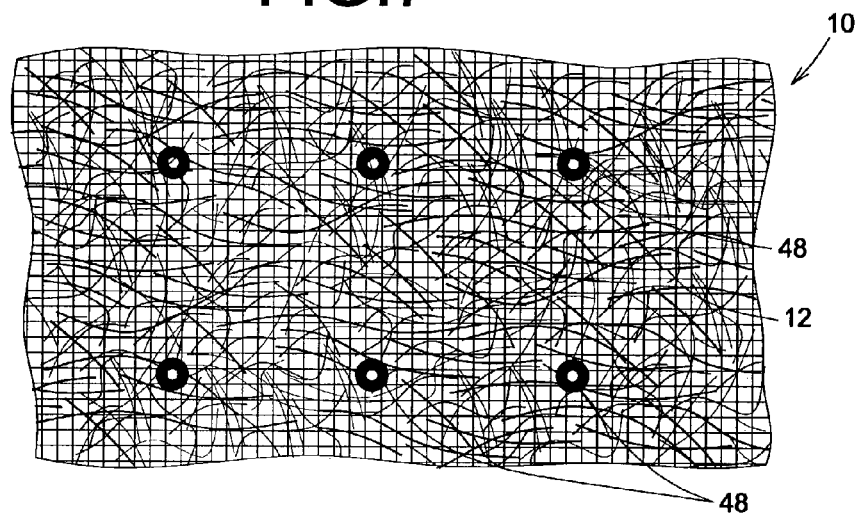
FIG. 8 is a simplified front view of an alternative filter for use with the system of FIG. 5, showing rivets as a fastening member.
Figure 9:
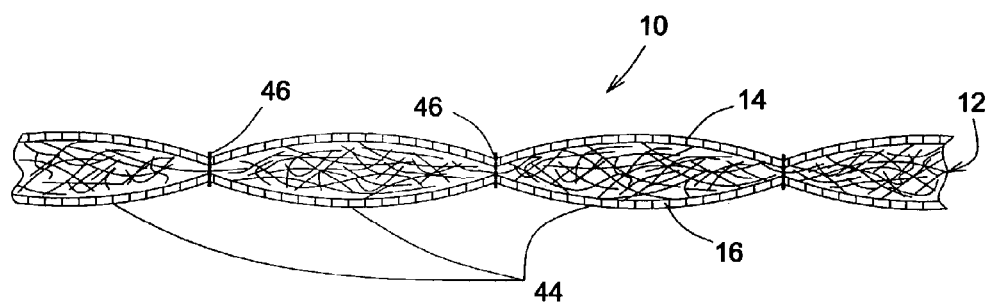
FIG. 9 is a cross sectional view taken along lines 9-9 of FIG. 7.

Referring now to FIGS. 5, 7, 8 and 9, other types of fastening members 32 are illustrated. One preferable type of fastening member 32 includes a plurality of stitches 46 which may be arranged in a variety of patterns, for example wavy lines or straight lines. The stitches 46 pass through the network 12 and divide the network into subdivisions 44, as previously described. Alternatively, as best illustrated in FIG. 8, the fastening members 32 may also include rivets 48, which pass through the network 12.

EXAMPLES

The present invention is illustrated in further detail by the following non-limiting examples.

Example 1

Evaluation of Microbicidal and Filtering Capacity of Rigid and Soft Facemasks

As shown in Table 1, two facemasks of the present invention were compared to a commercially available facemask[1,2,3] for their antimicrobial and retaining capabilities against a panel of bacteria and molds of various sizes[4,5,6,7]. The NB rigid and soft masks used in Examples 1 and 2 were both equipped with a network 12 of PVC organic fiber containing TRICLOSAN™. The NB soft mask was composed of a double covering of woven type fabric containing 76% w/w THERMOVYL-ZCB™ fibers and 24% w/w polyester (although any other woven type fabric such as cotton or the like could have been used) stitched to each other at their periphery, within which the network 12 was located (see FIG. 2a above). The NB rigid mask was made of two conventional commercially available anti-dust masks, which were inserted one inside the other, between which the network of PVC organic fiber containing TRICLOSAN™ was located.

An air contamination chamber[5,8,9] was used to measure the filtering capacity of a mask containing the network. The chamber includes a perforated bottle containing a predetermined quantity of lyophilized microorganisms. The chamber is installed on a microbiologic air-sampler. The test mask was installed at the interface between the contaminated air chamber and the air sampler. A negative pressure was generated in the air chamber, which caused the lyophilized microorganisms to move towards the mask. A culturing medium was located downstream of the mask to detect any breakthrough of the mask.

TABLE 1

| | | Filtration efficiency (%) | | |
|---|---|---|---|---|
| Microorganisms | Size (µm) | NBRM | NBSM | 3M* |
| Bacteria | | | | |
| Mycobacteria tuberculosis | 0.2-0.7 × 1.0-10 | 100 | 100 | 95 |
| Proteus spp. | 0.4-0.8 × 1-3 | 100 | 100 | |
| Pseudomonas aureginosa | 0.5-1.0 × 1.5-5 | 100 | 100 | |

TABLE 1-continued

| Microorganisms | Size (μm) | Filtration efficiency (%) | | |
|---|---|---|---|---|
| | | NBRM | NBSM | 3M* |
| *Staphylococcus aureus* | 0.5 × 1.5 | 100 | 100 | |
| *Streptococcus pneumoniae* | 0.5-1.5 | 100 | 100 | |
| *Haemophilus influenze* | 1 | 100 | 100 | |
| Anthrax | 1-1.5 × 3-5 | 100 | 100 | |
| Moulds | | | | |
| *Acremonium strictum* | 3.3-5.5 (7) × 0.9 × 1.8 | 100 | 100 | 96 |
| *Aspergillus versicolor* | 2-3.5 | 100 | 100 | |
| *Penicillium griseofulvum* | 2.5-3.5 × 2.2-2.5 | 100 | 100 | |
| *Neosartorya fischeri* | 2 × 2.5 | 100 | 100 | |

NBRM = Rigid mask
NBSM = Soft mask
*Data from technical specification[2]

Example 2

Evaluation of Filtering of Small Particles

The filtering capacity of the three masks of Example 1 was tested against two particulate materials of 0.3 μm particle size using essentially the same apparatus as in Example 1. A cartridge capturing membrane located downstream from an air pump, in this case, captured breakthrough particulates. The air pump creates a negative pressure downstream of the mask. The two particulate materials chosen were sodium chloride and dioctyl phthalate.

TABLE 2

| Particulate material | Size (μm) | Filtration efficiency (%) | | |
|---|---|---|---|---|
| | | NBRM | NBSM | 3M* |
| Sodium chloride (NaCl) | 0.3 | 100 | 100 | 95 |
| Dioctylphthalate (DOP) | 0.3 | 100 | 100 | |

NBRM = Rigid mask
NBSM = Soft mask
*Data from technical specification[2]

Example 3

Evaluation of Microbicidal and Filtering Capacity of a Ventilation System Filter The antimicrobial capacity of a filter of the embodiment of FIG. 3 with RHOVYL'A.S.+™ fibers was evaluated after 0, 7, 14, and 21 days installation in a ventilation system in a house. The results are illustrated in Tables 3 to 6 below.

The filters were removed after the aforesaid times and analysed using the Samson method[10]. The fibrous material (1 g) of each filter was diluted with demineralised, sterilized water (9 mL) and then serially diluted.

The calculation of total amount of bacteria, yeast and molds were done using hemacytometry. The calculation of the total amount of viable bacteria, yeasts and molds were determined following a culture of the serial dilutions on appropriate media. The aerobic viable bacteria were cultured on soya agar-agar (TSA, Quelab), whereas the yeasts and molds were cultured on HEA supplemented with gentamycin (0.005% p/v) and oxytetracycline (0.01% p/v) to limit bacterial growth. HEA's pH of 4.8+/−0.2 allows the germination of spores and development of mycelens. After the incubation period, the calculation of microbial colonies was carried out using a colony meter (Accu-Lite™, Fisher). The morphotype of the bacterial colonies was identified by Gram staining (see Table 5).

Concerning the yeasts and molds calculation, each macroscopically distinct mold colony was identified by gender and/or species using microscopy.

Mold slides were prepared using the adhesive tape method[11]. This technique maintains the integrity of the mold structures by fixing them on the sticky side of the tape. Once collected, the molds were stained with lactophenol and observed at a magnification of 10× and 40×. Using identification keys[12,13,14,15], the molds were identified. In this experiment only colonies that produced spores were identified.

TABLE 3

| After filter | Bacterial filtering | | |
|---|---|---|---|
| | Calculated bacteria (UFC/g) | | |
| Time (days) | Viable | Non-viable | Total |
| 0 | 6000 (3.43%) | 169000 (96.57%) | 175000 (100%) |
| 7 | 9000 (2.75%) | 318000 (97.25%) | 327000 (100%) |
| 14 | 27000 (2.21%) | 1193000 (97.79%) | 1220000 (100%) |
| 21 | 70000 (1.88%) | 3650000 (98.12%) | 3720000 (100%) |

TABLE 4

| After filter | Fungal filtering | | |
|---|---|---|---|
| | Calculated fungi (UFC/g) | | |
| Time (days) | Viable | Non-viable | Total |
| 0 | 29000 (11.74%) | 218000 (88.26%) | 247000 (100%) |
| 7 | 110000 (10.19%) | 970000 (89.81%) | 1080000 (100%) |
| 14 | 230000 (8.75%) | 2400000 (91.25%) | 2630000 (100%) |
| 21 | 1640000 (7.24%) | 21000000 (92.76%) | 22640000 (100%) |

TABLE 5

| Identification of bacterial morphotypes | |
|---|---|
| After filter (days) | Bacterial morphotypes |
| 0 | 78.4% Cocci Gram positive |
| | 21.6% Rod Gram negative |
| 7 | 84.3% Cocci Gram positive |
| | 15.7% Rod Gram negative |
| 14 | 86.7% Cocci Gram positive |
| | 13.3% Rod Gram negative |
| 21 | 88.9% Cocci Gram positive |
| | 11.1% Rod Gram negative |

TABLE 6

Identification of mold species

| After filter (days) | Mold species |
| --- | --- |
| 0 | *Aspergillus niger, Cladosporium cladosporioides, Cladosporium herbarum, Penicillium* sp., yeasts |
| 7 | *Aspergillus niger, Cladosporium cladosporioides, Cladosporium herbarum, Penicillium* sp., yeasts |
| 14 | *Alternaria alternata,* Arthrinium sp., *Aspergillus niger,* Cladosporium sp., Geotrichum sp., *Penicillium* sp., yeasts |
| 21 | *Aspergillus niger, Cladosporium cladosporioides, Cladosporium herbarum, Penicillium* sp., yeasts |

Discussion

To date, commercially available masks have been hampered by their inability to capture and kill in excess of 95% of microorganisms. A study of a microbicidal network of the present invention, in the form of the facemasks and filters in a ventilation system, has demonstrated a significant improvement in capturing and killing efficiency (Tables 1 to 6).

Tables 1 and 2 illustrated the effectiveness of PVC organic fiber containing TRICLOSAN™ as particulate filters, anti-bacterial and anti-mold filters. For both the soft facemask and the rigid facemask, the anti-microbial and particulate filtering capacities were 100% compared to the corresponding capacities for a commercially available mask (95 to 96%).

Tables 3 to 6 illustrate highly efficient levels of antimicrobial and filtering capacity of the filter of the present invention. Specifically, the inventor has demonstrated, in Tables 3 and 4, that the combined anti-bacterial, anti-fungal, and retaining capacities are each 100%.

In addition, the inventor has demonstrated that different bacterial morphotypes, as is illustrated in Table 5, were captured on the filter after zero (0) days 96.6% (78.8% and 21.6% of cocci Gram-positive and rod Gram-negative type bacteria respectively) of the whole bacteria population present on the fibers of the filter. After twenty-one days (21) 98.1% (88.9% and 11.1% of cocci Gram-positive and rod Gram-negative type bacteria respectively) were present on the fibers of the filter. This demonstrates that the efficiency of the filer remains after an extended period. As illustrated in Table 6, a variety of pathogenic molds were identified on the filter of the present invention up to twenty-one days.

If desired, the filter can be cleaned and reused without a significant loss of the aforesaid capacities (results not shown).

A key feature of the filter 10, whether it be in the aforesaid facemasks or the circulation system duct filter, is its ability to immobilize, retain and kill or inhibit the growth of a wide variety of microbes, which come into contact with the network 12 of fibers 20. Air that is either pre-filtered, in the case of the circulation system, or inhaled/exhaled through the facemask by the user, often includes residual microbes that have either passed through the primary filter or the filter has failed to immobilize them. In the case where a person who uses the facemask of the present invention and who has an upper respiratory infection, such as influenza, tuberculosis, anthrax, severe acute respiratory syndrome (SARS) and the like, can significantly reduce or essentially eliminate further infection to other people. Similarly, air that is contaminated with pathogenic microbes can be filtered before entering into the nose and mouth area of the user. The flow of air is shown by the arrows in FIGS. 2, 2a, and 5, in which air contaminated with microbes is shown as hatched lines and non-hatched arrows show clean, filtered air.

REFERENCES (INCORPORATED HEREIN BY REFERENCE)

1. National Institute for Occupational Safety and Health. NIOSH respirator decision logic. Cincinnati, Ohio: Department of Health and Human Services, Public Health service, CDC, 1987:13-9; DHHS publication no. (NIOSH) 87-108.
2. TB Respiratory Protection Program In Health Care Facilities Administrator's Guide, (http://www.cdc.gov/niosh/99-143.html).
3. 3M Soins de santé Canada; Une protection fiable a chaque respiration; 3M® 2002.
4. MMWR; Laboratory Performance Evaluation of N95 Filtering Facepiece Respirators, 1996 (Dec. 11, 1998).
5. Edwin H. Lennette, Albert Balows, William J. Hausler, Jr. H. Jean Shadomy, 1985, Manual of Clinical Microbiology.
6. Robert A. Samson, Ellen S. van Reenen-Hoekstra, 1990, Introduction to food-borne Fungi.
7. G. Nolt, Noel R. Krieg, Peter H. A. Sneath, James T. Staley, Stanley, T. Williams, 1994, Bergey's Manual of Determinative bacteriology.
8. Fradkin A (1987) Sampling of microbiological contaminants in indoor air, In: sampling and calibration for atmospheric measurements ASTM Special Technical Publication, 957:66-77.
9. 42 CFR Part 84 Respiratory Protective Devices, (http://www.cdc.gov/niosh/pt84abs2.html).
10. Samson, R A. 1985. *Air sampling methods for biological contaminants*. Document de travail fourni au Groupe sur les champignons dans l'air des maisons de Santé et Bien-être social Canada, Ottawa, Ontario, K1A 1L2.
11. Koneman, W. E. et G. D. Roberts. 1985. Practical laboratory mycology 3rd ed. Williams and Wilkins. Baltimore, Md.
12. Domsch, K. H., W. Gams et T.-H. Anderson. 1980. Compendium of soil fungi. Academic Press. London.
13. Larone, D. H. 1987. Medically important fungi. A guide to identification. New York. Elsevier Science Publishing Co. Inc.
14. Malloch, D. 1981. Moulds, their isolation, cultivation and identification. Toronto: University of Toronto Press. 97 p.
15. St-Germain, G. et R. C. Summerbell. 1996. Champignons filamenteux d'intérêt médical: Caractéristiques et identification. Star Publishing Company. Belmont, Calif.

I claim:

1. A microbicidal air filter for use with an air passageway, said air filter comprising:
   an immobilization network for retaining immobilized and killed microbes,
       said network including fibers in which each of said fibers has a fiber body having an amount of at least one antimicrobial agent sufficient to substantially immobilize, retain and kill microbes suspended in a volume of air moving through said air passageway,
   wherein said fibers substantially incorporate said antimicrobial agent throughout each of said fiber body; and
   said immobilization network being substantially permeable to said air.

2. The filter, according to claim 1, in which said immobilization network includes a plurality of fibers arranged in a mesh, said mesh defining a plurality of air spaces between said fibers.

3. The filter, according to claim 2, wherein said antimicrobial agent is integral with each said fiber body.

4. The filter, according to claim 3, in which said fibers are tightly woven or loosely woven.

5. The filter, according to claim 4, in which said fibers include treated fibers.

6. The filter, according to claim 3, in which said antimicrobial agent is selected from the group consisting of: an antibacterial agent, an anti-viral agent, an anti-dust mite agent, an anti-mold agent and an anti-yeast agent.

7. The filter, according to claim 6, in which said antimicrobial agent is benzyl benzoate.

8. The filter, according to claim 1, in which said air is pre-filtered.

9. The filter, according to claim 1, in which said air filter is a facemask configured and sized to fit over the nose and mouth of a user and to be secured therearound.

10. The filter, according to claim 1, in which said air filter is an air duct filter configured and sized to fit in an air duct system.

11. A microbicidal air filter for use with an air passageway, said air filter comprising:
   an immobilization network for retaining immobilized and growth inhibited microbes,
      said network including fibers having fiber bodies each having therein an amount of at least one antimicrobial agent integrated throughout said fiber bodies sufficient to substantially immobilize, retain and substantially inhibit the growth of microbes suspended in a volume of air moving through said air passageway,
   said immobilization network being substantially permeable to said air.

12. The filter, according to claim 11, in which said immobilization network includes a plurality of fibers arranged in a mesh, said mesh defining a plurality of air spaces between said fibers.

13. The filter, according to claim 12, in which each of said fibers has a fiber body in which said antimicrobial agent is permanently incorporated throughout said fiber body.

14. The filter, according to claim 13, in which said fibers are tightly woven or loosely woven.

15. The filter, according to claim 14, in which said fibers include treated fibers.

16. The filter, according to claim 13, in which said antimicrobial agent is selected from the group consisting of: an antibacterial agent, an anti-viral agent, an anti-dust mite agent, an anti-mold agent and an anti-yeast agent.

17. The filter, according to claim 16, in which said antimicrobial agent is benzyl benzoate.

18. The filter, according to claim 11, in which said air is pre-filtered.

19. The filter, according to claim 11, in which said air filter is a facemask configured and sized to fit over the nose and mouth of a user and to be secured therearound.

20. The filter, according to claim 11, in which said air filter is an air duct filter configured and sized to fit in an air duct system.

21. A microbicidal facemask comprising: first and second air permeable screen elements secured together along respective peripheral edges, said screen elements defining a gap therebetween, said screen elements being configured and sized to fit over the mouth and nose of a user and to be secured thereto; an air permeable immobilization network located in and substantially filling said gap, said immobilization network for retaining immobilized and killed microbes, said network including fibers each having a fiber body having an amount of at least one antimicrobial agent integrated throughout said fiber body sufficient to substantially immobilize, retain and kill microbes suspended in a volume of air moving through said network.

22. The facemask, according to claim 21, in which said immobilization network includes a plurality of fibers arranged in a mesh, said mesh defining a plurality of air spaces between said fibers.

23. The facemask, according to claim 22, in which said antimicrobial agent is substantially permanently integrated throughout said fiber body.

24. The facemask, according to claim 23, in which said fibers are tightly woven or loosely woven.

25. The facemask, according to claim 24, in which said fibers include treated fibers.

26. The facemask, according to claim 23, in which said antimicrobial agent is selected from the group consisting of: an antibacterial agent, an anti-viral agent, an anti-dust mite agent, an anti-mold agent and an anti-yeast agent.

27. The facemask, according to claim 26, in which said antimicrobial agent is benzyl benzoate.

28. The facemask, according to claim 21, in which said air is pre-filtered.

29. The facemask, according to claim 21, in which said first air permeable screen element includes a slit located therein of sufficient size to allow said immobilization network to be positioned in said gap.

30. A microbicidal facemask comprising:
   first and second air permeable screen elements secured together along respective peripheral edges, said screen elements defining a gap therebetween, said screen elements being configured and sized to fit over the mouth and nose of a user and to be secured thereto; an air permeable immobilization network located in and substantially filling said gap, said immobilization network for retaining immobilized and growth inhibited microbes, said network including fibers each having a fiber body with an amount of at least one antimicrobial agent permeated throughout each fiber body sufficient to substantially immobilize, retain and substantially inhibit the growth of microbes suspended in a volume of air moving through said network.

31. The facemask, according to claim 30, in which said immobilization network includes a plurality of fibers arranged in a mesh, said mesh defining a plurality of air spaces between said fibers.

32. The facemask, according to claim 31, in which said antimicrobial agent is substantially permanently permeated throughout each fiber body.

33. The facemask, according to claim 32, in which said fibers are tightly woven or loosely woven.

34. The facemask, according to claim 33, in which said fibers include treated fibers.

35. The facemask, according to claim 32, in which said antimicrobial agent is selected from the group consisting of: an antibacterial agent, an anti-viral agent, an anti-dust mite agent, an anti-mold agent and an anti-yeast agent.

36. The facemask, according to claim 35, in which said antimicrobial agent is benzyl benzoate.

37. The facemask, according to claim 30, in which said air is pre-filtered.

38. The facemask, according to claim 30, in which said first air permeable screen element includes a slit located therein of sufficient size to allow said immobilization network to be positioned in said gap.

39. A microbicidal air duct filter for use in an air circulation system, said air duct filter comprising: first and second air permeable screen elements securable together along respective peripheral edges, said screen elements being configured and sized to fit in an air duct and to be secured therein; an air permeable immobilization network located substantially between said first and second screen elements, said immobilization network for retaining immobilized and killed microbes, said network including fibers each having a fiber body with an amount of at least one antimicrobial agent incorporated throughout each of said fiber body sufficient to substantially immobilize, retain and kill microbes suspended in a volume of air moving through said network.

40. The air duct filter, according to claim 39, in which said immobilization network includes a plurality of fibers arranged in a mesh, said mesh defining a plurality of air spaces between said fibers.

41. The air duct filter, according to claim 40, in which said antimicrobial agent is substantially permanently incorporated throughout each of said fiber body.

42. The air duct filter, according to claim 41, in which said fibers are tightly woven or loosely woven.

43. The air duct filter, according to claim 42, in which said fibers include treated fibers.

44. The air duct filter, according to claim 41, in which said antimicrobial agent is selected from the group consisting of: an antibacterial agent, an anti-viral agent, an anti-dust mite agent, an anti-mold agent and an anti-yeast agent.

45. The air duct filter, according to claim 44, in which said antimicrobial agent is benzyl benzoate.

46. The air duct filter, according to claim 39, in which a fastening member connects said first and second air permeable screen elements together to sandwich said immobilization network therebetween.

47. The air duct filter, according to claim 46, in which said fastening member includes a frame for connecting said first and second screen elements together.

48. The air duct filter, according to claim 39, in which said air is pre-filtered.

49. A microbicidal air duct filter for use in an air circulation system, said air duct filter comprising: first and second air permeable screen elements securable together along respective peripheral edges, said screen elements being configured and sized to fit in an air duct and to be secured therein; an air permeable immobilization network located substantially between said first and second screen elements, said immobilization for retaining immobilized and growth inhibited microbes, said network including fibers each having a fiber body with an amount of at least one antimicrobial agent integrated throughout said fiber body sufficient to substantially immobilize, retain and substantially inhibit the growth of microbes suspended in a volume of air moving through said network.

50. The air duct filter, according to claim 49, in which said immobilization network includes a plurality of fibers arranged in a mesh, said mesh defining a plurality of air spaces between said fibers.

51. The air duct filter, according to claim 50, in which said antimicrobial agent is permanently integrated throughout said fiber body.

52. The air duct filter, according to claim 51, in which said fibers are tightly woven or loosely woven.

53. The air duct filter, according to claim 52, in which said fibers include treated fibers.

54. The air duct filter, according to claim 51, in which said antimicrobial agent is selected from the group consisting of: an antibacterial agent, an anti-viral agent, an anti-dust mite agent, an anti-mold agent and an anti-yeast agent.

55. The air duct filter, according to claim 54, in which said antimicrobial agent is benzyl benzoate.

56. The air duct filter, according to claim 49, in which a fastening member connects said first and second air permeable screen elements together to sandwich said immobilization network therebetween.

57. The air duct filter, according to claim 56, in which said fastening member includes a frame for connecting said first and second screen elements together.

58. The air duct filter, according to claim 49, in which said air is pre-filtered.

59. The air filter, according to claim 11, in which said immobilization network is a fibrous material.

60. The facemask, according to claim 30, in which said immobilization network is a fibrous material.

61. The air duct filter, according to claim 39, in which said immobilization network is a fibrous material.

62. The air filter, according to claim 11, in which said immobilization network captures and retains said microbes in said network.

63. The facemask, according to claim 21, in which said immobilization network captures and retains said microbes in said network.

64. The air duct filter, according to claim 49, in which said immobilization network captures and retains said microbes in said network.

65. A microbicidal air filter for use with an air passageway, said air filter comprising:
   an immobilization network for retaining immobilized and killed microbes,
      said network including fibers each having a fiber body having an amount of at least one antimicrobial agent substantially permeated throughout the fiber body sufficient to substantially immobilize, retain and kill microbes suspended in a volume of air moving through said air passageway,
   said immobilization network being substantially permeable to said air.

66. A microbicidal air filter for use with an air passageway, said air filter comprising:
   an immobilization network for retaining immobilized and growth inhibited microbes, said network including fibers each having a fiber body having an amount of at least one antimicrobial agent substantially permeated throughout the fiber body sufficient to substantially immobilize, retain and inhibit the growth of microbes suspended in a volume of air moving through said air passageway, said immobilization network being substantially permeable to said air.

67. A microbicidal air filter for use with an air passageway, said air filter comprising:

an immobilization network for retaining immobilized and killed microbes, said network including fibers having substantially and permanently impregnated therein an amount of at least one antimicrobial agent sufficient to substantially immobilize, retain and kill microbes suspended in a volume of air moving through said air passageway, said immobilization network being substantially permeable to said air.

68. A microbicidal air filter for use with an air passageway, said air filter comprising:

an immobilization network for retaining immobilized and growth inhibited microbes, said network including fibers having substantially permanently and impregnated therein an amount of at least one antimicrobial agent sufficient to substantially immobilize, retain and inhibit the growth of microbes suspended in a volume of air moving through said air passageway, said immobilization network being substantially permeable to said air.

* * * * *

UNITED STATES PATENT AND TRADEMARK OFFICE
CERTIFICATE OF CORRECTION

Page 1 of 2

PATENT NO. : 7,559,968 B2
APPLICATION NO. : 10/455337
DATED : July 14, 2009
INVENTOR(S) : Normand Bolduc It is certified that error appears in the above-identified patent and that said Letters Patent is hereby corrected as shown below:

Column 2, line 51, delete "suspended In a volume" and insert --suspended in a volume--.

Column 4, line 57, delete "impregnated therein, (embodied) therein," and insert --impregnated (embodied) therein,--.

Column 5, lines 40-41, delete "work yet, don't" and insert --work, yet don't--.

Columns 6 and 7, Table 1, delete

TABLE 2

| Microorganisms | Size (μm) | Filtration efficiency (%) | | |
| --- | --- | --- | --- | --- |
| | | NBRM | NBSM | 3M* |
| Bacteria | | | | |
| Mycobacteria tuberculosis | 0.2-0.7 x 1.0-10 | 100 | 100 | 95 |
| Proteus spp. | 0.4-0.8 x 1-3 | 100 | 100 | |
| Pseudomonas aureginosa | 0.5-1.0 x 1.5-5 | 100 | 100 | |
| Staphylococcus aureus | 0.5 x 1.5 | 100 | 100 | |
| Streptococcus pneumonia | 0.5-1.5 | 100 | 100 | |
| Haemophilius influenze | 1 | 100 | 100 | |
| Anthrax | 1-1.5 x 3-5 | 100 | 100 | |
| Moulds | | 100 | 100 | |
| Acremonium strictum | 3.3-5.5 (7) x 0.9 x 1.8 | 100 | 100 | 96 |
| Aspergillus versicolor | 2-3.5 | 100 | 100 | |
| Penicillium griseofulvum | 2.5-3.5 x 2.2-2.5 | 100 | 100 | |
| Neosartorya fischeri | 2 x 2.5 | 100 | 100 | |

NBRM = Rigid mask
NBSM = Soft mask
" *Data from technical specification² "

and insert

Signed and Sealed this
First Day of March, 2011

David J. Kappos
*Director of the United States Patent and Trademark Office*

TABLE 2

| Microorganisms | Size (µm) | Filtration efficiency (%) | | |
|---|---|---|---|---|
| | | NBRM | NBSM | 3M* |
| Bacteria | | | | |
| Mycobacteria tuberculosis | 0.2-0.7 x 1.0-10 | 100 | 100 | 95 |
| Proteus spp. | 0.4-0.8 x 1-3 | 100 | 100 | 95 |
| Pseudomonas aureginosa | 0.5-1.0 x 1.5-5 | 100 | 100 | 95 |
| Staphylococcus aureus | 0.5 x 1.5 | 100 | 100 | 95 |
| Streptococcus pneumonia | 0.5-1.5 | 100 | 100 | 95 |
| Haemophilius influenze | 1 | 100 | 100 | 95 |
| Anthrax | 1-1.5 x 3-5 | 100 | 100 | 95 |
| Moulds | | | | |
| Acremonium strictum | 3.3-5.5 (7) x 0.9 x 1.8 | 100 | 100 | 96 |
| Aspergillus versicolor | 2-3.5 | 100 | 100 | 96 |
| Penicillium griseofulvum | 2.5-3.5 x 2.2-2.5 | 100 | 100 | 96 |
| Neosartorya fischeri | 2 x 2.5 | 100 | 100 | 96 |

NBRM = Rigid mask
NBSM = Soft mask
*Data from technical specification[2]

Column 7, Table 2, delete

TABLE 2

| Particulate material | Size (µm) | Filtration efficiency (%) | | |
|---|---|---|---|---|
| | | NBRM | NBSM | 3M* |
| Sodium chloride (NaCl) | 0.3 | 100 | 100 | 95 |
| Dioctylphthalate (DOP) | 0.3 | 100 | 100 | |

NBRM = Rigid mask
NBSM = Soft mask
*Data from technical specification[2]

" and insert

TABLE 2

| Particulate material | Size (µm) | Filtration efficiency (%) | | |
|---|---|---|---|---|
| | | NBRM | NBSM | 3M* |
| Sodium chloride (NaCl) | 0.3 | 100 | 100 | 95 |
| Dioctyl Phthalate (DOP) | 0.3 | 100 | 100 | 95 |

NBRM = Rigid mask
NBSM = Soft mask
*Data from technical specification[2]

Column 9, line 42, delete "population present" and insert --population were present--.

Column 9, line 67, delete "like, can significantly" and insert --like, the facemask can significantly--.